(12) United States Patent
Govindarajan et al.

(10) Patent No.: US 7,479,499 B2
(45) Date of Patent: Jan. 20, 2009

(54) METHODS OF USING THALIDOMIDE IN COMBINATION WITH IRINOTECAN

(75) Inventors: Rangaswamy Govindarajan, Little Rock, AR (US); Andrew Zeitlin, Basking Ridge, NJ (US)

(73) Assignees: Celgene Corporation, Summit, NJ (US); Board of Trustees of the University of Arkansas, Little Rock, AK (US)

( * ) Notice: Subject to any disclaimer, the term of this patent is extended or adjusted under 35 U.S.C. 154(b) by 625 days.

(21) Appl. No.: 11/126,315

(22) Filed: May 11, 2005

(65) Prior Publication Data

US 2005/0203060 A1 Sep. 15, 2005

Related U.S. Application Data

(62) Division of application No. 09/853,619, filed on May 14, 2001, now Pat. No. 6,914,067.

(60) Provisional application No. 60/204,142, filed on May 15, 2000.

(51) Int. Cl.
*A61K 31/445* (2006.01)
(52) U.S. Cl. ..................................... 514/323
(58) Field of Classification Search ....................... None
See application file for complete search history.

(56) References Cited

U.S. PATENT DOCUMENTS

| 4,604,463 A | 8/1986 | Miyasaka et al. | 544/125 |
| 5,385,901 A | 1/1995 | Kaplan et al. | 514/231.5 |
| 5,593,990 A | 1/1997 | D'Amato | 514/235.2 |
| 5,629,327 A | 5/1997 | D'Amato | 514/323 |
| 5,643,915 A | 7/1997 | Andrulis, Jr. et al. | 514/279 |
| 5,654,312 A | 8/1997 | Andrulis, Jr. et al. | 514/279 |
| 5,712,291 A | 1/1998 | D'Amato | 514/323 |

FOREIGN PATENT DOCUMENTS

WO  WO 94/20085  9/1994

OTHER PUBLICATIONS

Online Merriam Webster Dictionary, http://www.merriam-webster.com/dictionary/eliminate; accessed Mar. 12, 2008.*
Burton et al. Current Opinion in Oncology, 1999, vol. 13, No. 3, p. 157 (6 HTML pages attached).*
Avgeropoulos et al., *The Oncologist* 4:209-224 (1999).
Bach et al., *Acta Pathol. Microbiol. Scand.* 59:491-499 (1963).
Bach et al., *The Lancet* 71:1271 (1963).
Braun et al., *Biochem. Biophys. Res. Comm.* 98(4):1029-1034 (1981).
Chaundry et al., *Cancer Res.* 26:1884-1886 (1966).
Costa et al., *Blood* 92 (10:suppl. 1):235b (1998).
Cunningham et al., *The Lancet* 352(9138):1413-1418 (1998).
D'Amato et al., *Proc. Natl. Acad. Sci.* 91:4082-4085 (1994).
De et al., *J. Pharm. Sci.* 64(2):262-266 (1975).
DiPaolo et al., *Proc. Soc. Exp. Biol. And Med.* 114:384-387 (1963).
DiPaolo et al., *Science* Jun. 26, 1964:1583 (1964).
DiPaolo et al., *Cancer Chemo. Reports* 29:99-102 (1963).
Ehrenpreis et al., *Gastroenterology* 117:1271-1277 (1999).
Gershbein,*Riv. Pathol. Nerv. Ment.* 87(4):88-92 (1966).
Grabstald et al., *Clin. Pharmacol. And Ther.* 6(3):298-302 (1965).
Hatfill et al., *Leuk. Res* 15(2-3):129-136 (1991).
Koch, *Prog. Med. Chem.* 22:165-242 (1985).
Lenicque *Acta Zool.* 48:128-139 (1967).
Marx et al., *Proc. Am. Soc. Clin. Oncology* 18:154a (1999).
McCann, *Drug Topics* 41-42 (Jun. 21, 1999).
McHugh et al., *Clin. Exper. Immunol.*, 99:160-167 (1995).
Miura et al., *Experientia* 26:305-306 (1970).
Mohri et al., *Chem. Pharm. Bull.* 16:2289-2292 (1968).
Moller et al., *J. Immunol.* 159:5157-5161 (1997).
Moreira et al., *J. Expr. Med.* 177:1675-1680 (1993).
Muckter, *Antimicrobial Agents and Chemotherapy* 531-538 (1965).
Mummery et al., *Toxicol. Lett.* 18(3):201-209 (1983).
Olson et al., *Clin. Pharmacol. And Ther.* 6:293-297 (1965).
*Physician's Desk Reference*, 2412-2418 (54th ed., 2000).
*Physician's Desk Reference*, 911-916 (54th ed., 2000).
Pitot et al., *J. Clin. Oncology* 15(8):2910-2919 (1997).
Robbins et al., *Basic Pathology*, 2nd ed., W.B. Saunsers Co., Philadelphia, pp. 68-79 (1976).
Roe et al., *Nature* 200:1016-1017 (1963).
Rothenberg, *Annals of Oncology* 8:837-855 (1997).
Rothenberg et al., *Cancer* 85(4):786-795 (1999).
Rothenberg et al., *J. Clin. Oncology* 14(4):1128-1135 (1996).
Singhal et al., *New England J. Med.* 341(21):1565-1571 (1999).
Sugiura et al., *GANN* 55:57-60 (1964).
Vasiliauskas et al., *Gastroenterology* 117:1278-1287 (1999).
Villa et al., *Haematol. Latina* 6:217-221 (1963).
Villa et al., *The Lancet*, Mar. 30, 1963, 725 (1963).
Woodyatt, *The Lancet*, Apr. 7, 1962, 750 (1962).
Zwart, *Arzneim-Forsch.* 16(12):1688-1689 (1966).

* cited by examiner

*Primary Examiner*—Ardin Marschel
*Assistant Examiner*—James D Anderson
(74) *Attorney, Agent, or Firm*—Jones Day

(57) ABSTRACT

This invention relates to compositions comprising thalidomide and irinotecan, which can be used in the treatment or prevention of colorectal cancer. The invention also relates to methods of treating or preventing colorectal cancer which comprise the administration of thalidomide and irinotecan to a patient in need of such treatment or prevention. The invention further relates to methods of reducing or avoiding adverse side effects associated with the administration of irinotecan which comprise the administration of thalidomide to a patient in need of such reduction or avoidance.

3 Claims, No Drawings

METHODS OF USING THALIDOMIDE IN COMBINATION WITH IRINOTECAN

This application is a division of U.S. application Ser. No. 09/853,619, filed May 14, 2001, now U.S. Pat. No. 6,914,067, which claims priority to U.S. Provisional Application No. 60/204,142, filed May 15, 2000, both of which are incorporated herein in their entireties by reference.

1. FIELD OF THE INVENTION

This invention relates to pharmaceutical compositions comprising thalidomide and irinotecan, to methods of treating colorectal cancer, and to methods of reducing or avoiding adverse effects of irinotecan.

2. BACKGROUND OF THE INVENTION

2.1. Colorectal Cancer

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor preneoplastic changes, which may under certain conditions progress to neoplasia.

Pre-malignant abnormal cell growth is exemplified by hyperplasia, metaplasia, or most particularly, dysplasia (for review of such abnormal growth conditions, see Robbins and Angell, 1976, *Basic Pathology*, 2d Ed., W. B. Saunders Co., Philadelphia, pp. 68-79). Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

The neoplastic lesion may evolve clonally and develop an increasing capacity for invasion, growth, metastasis, and heterogeneity, especially under conditions in which the neoplastic cells escape the host's immune surveillance. Roitt, I., Brostoff, J and Kale, D., *Immunology*, 17.1-17.12 (3rd ed., Mosby, St. Louis: 1993).

In Western countries, cancers of the colon and rectum account for more new cases of cancer than those of any other anatomic site except the lung. *The Merck Manual* 852 (16th ed. 1992). Most colorectal cancers are adenocarcinomas. In 1999, the incidence of colorectal cancer in the United States was 129,400 cases.

Despite the enormous number of deaths attributed to colorectal cancers, their specific mechanism remains unknown. It is known, however, that cancers of the colon and rectum spread in at least five ways: directed extension through the bowel wall; hematogenous metastases; regional lymph node metastases; perineural spread; and intraluminal metastases. Id.

Primary treatment of colorectal cancers typically includes surgery. Many patients, however, must also be treated with a combination of radiation and chemotherapy. As of 1992, the most effective chemotherapy regime consisted of the administration of 5-fluorouracil (5FU) and methyl-CCNU. Id. But while 5FU has been the drug of choice in the treatment of metastatic colorectal cancer for several decades, partial responses occur in less than 25 percent of patients and complete responses are extremely rare. Patients who progress after 5FU therapy are usually treated with the DNA topoisomerase I inhibitor CPT-11 (irinotecan), the only drug currently approved in the US for second line treatment of colorectal cancer. Overall response rates for CPT-11 are less than 20 percent, however, and complete response is achieved in less than one percent. The median duration of response is only 6.4 months. See, e.g., Rothenberg M L, et al., *Cancer* 85(4): 786-795 (1999); and Cunningham, D, et al., *The Lancet* 352 (9138):1413-1418 (1998).

The main dose-limiting factor of CPT-11 is severe and frequent gastrointestinal (GI) toxicity, particularly diarrhea, which may be early onset (within 24 hours of drug administration) or late onset (more than 24 hours after administration). Early onset diarrhea is uncommon, cholinergic in nature, and responds to atropine. In contrast, debilitating (Grade 3-4) late onset diarrhea occurs in 30-40 percent of patients and adversely affects their quality of life. Id. In nine to 30 percent of patients, the diarrhea does not respond to loperamide and thus may require hospitalization, dose modification, and/or interruption of chemotherapy. Id.

2.2. Irinotecan

Irinotecan, also referred to as CPT-11 and chemically named (4S)-4,11-diethyl-4-hydroxy-9-[(4-piperidino-piperidino)carbonyl-oxy]1H-pyranol-[3',4':6,7]indolizinol[1,2-b]quinoline-3,14-(4H,12H)dione, is described in U.S. Pat. No. 4,604,463. The hydrochloride trihydrate of irinotecan is sold under the tradename CAMPTOSAR®, and is indicated in the United States for the treatment of patients with metastatic carcinoma of the colon or rectum that recurred or progressed following 5-fluorouracil based therapy. *Physicians' Desk Reference*, 2412-2418 (54th ed., 2000). It has also recently been approved in the United States as a first-line therapy to treat patients with metastic colorectal cancer in combination with 5-fluorouracil and leucovorin. Irinotecan has also reportedly been used to treat other cancers, such as malignant gliomas and NSCLC. See, e.g., Avgeropoulos, N. G., and Batchelor, T. T., *The Oncologist* 4:209-224 (1999).

Irinotecan inhibits the activity of topoisomerases. Topoisomerases are enzymes that catalyze the relaxation of negatively supercoiled deoxyribonucleic acid (DNA). The process they catalyze is believed to comprise three steps: cleavage of one or both strands of a supercoiled DNA; passage of a segment of DNA through the break that is formed; and resealing of the break. Type I topoisomerases cleave one strand of DNA; type II topoisomerases cleave both strands. Stryer, L., *Biochemistry* 662-663 (3rd ed., 1988).

Because supercoiled double-stranded DNA must be unwound before processes such as replication, recombination, and transcription can occur, inhibition of the unwinding process can have dramatic consequences. For example, compounds that prevent or slow topoisomerase activity can be used to prevent cell growth and/or cause cell death. Such compounds, which are referred to as "topoisomerase inhibitors," have thus shown promise in the treatment of various types of cancer.

Irinotecan has numerous adverse effects, examples of which include, but are not limited to, early and late-forming diarrhea, nausea, vomiting, anorexia, constipation, flatulence, leukopenia, anemia, neutropenia, asthenia, abdominal cramping, fever, pain, loss of body weight, dehydration, alopecia, dyspnea, insomnia, and dizziness. See, e.g., *Physicians' Desk Reference*, 2415 (54$^{th}$ ed., 2000). The mechanisms by which these undesired effects occur are not well understood, but are believed to be different. In particular, the early and late-forms of diarrhea typically experienced by patients are reportedly mediated by different mechanisms. Id. But whatever their cause, the severity of one or more of their adverse effects limits the amount of irinotecan that can be administered to patients. The effectiveness of irinotecan is consequently limited not only by its ability to inhibit topoisomerase activity, but also by the severity and nature of its adverse effects.

Attempts have been made to alleviate adverse effects associated with irinotecan. For example, loperamide and the combination of loperamide and acetorphan have reportedly been administered to patients in an effort to reduce delayed-onset diarrhea. Rothenberg, M. L., *Annals of Oncology* 8:837-855 (1997). Unfortunately, these attempts met with limited success. Id.

2.3. Thalidomide

Thalidomide is a racemic compound sold under the tradename THALOMID® and chemically named α-(N-phthalimido)glutarimide or 2-(2,6-dioxo-3-piperidinyl)-1H-isoindole-1,3(2H)-dione. Thalidomide was originally developed in the 1950's to treat morning sickness, but due to its tetragenic effects was withdrawn from use. Thalidomide is now indicated in the United States for the acute treatment of the cutaneous manifestations of erythema nodosum leprosum. *Physicians' Desk Reference*, 911-916 (54$^{th}$ ed., 2000). Because its administration to pregnant women can cause birth defects, the sale of thalidomide is strictly controlled. Id.

In addition to treating symptoms of leprosy, thalidomide has reportedly been used to treat chronic graft-vs-host disease, rheumatoid arthritis, sarcoidosis, several inflammatory skin diseases, and inflammatory bowel disease. See generally, Koch, H. P., *Prog. Med. Chem.* 22:165-242 (1985). See also, Moller, D. R., et al., *J. Immunol.* 159:5157-5161 (1997); Vasiliauskas, E. A., et al., *Gastroenterology* 117:1278-1287 (1999); and Ehrenpreis, E. D., et al., *Gastroenterology* 117: 1271-1277 (1999). It has further been alleged that thalidomide can be combined with other drugs to treat iscehemia/reperfusion associated with coronary and cerebral occlusion. See U.S. Pat. No. 5,643,915, which is incorporated herein by reference.

Thalidomide has also reportedly been clinically investigated in the treatment of specific types of cancers. These include refractory multiple myeloma, brain, melanoma, breast, colon, mesothelioma, and renal cell carcinoma. See, e.g., Singhal, S., et al., *New England J. Med.* 341(21):1565-1571 (1999); and Marx, G. M., et al., *Proc. Am. Soc. Clin. Oncology* 18:454a (1999). It has further been reported that thalidomide can be used to prevent the development of chronic cardiomyopathy in rats caused by doxorubicin. Costa, P. T., et al., *Blood* 92(10:suppl. 1):235b (1998). Other reports concerning the use of thalidomide in the treatment of specific cancers include its combination with carboplatin in the treatment of glioblastoma multiforme. McCann, J., *Drug Topics* 41-42 (Jun. 21, 1999). Thalidomide has reportedly also been used as an antiemetic during the treatment of astrocytoma. Zwart, D., *Arzneim.-Forsch.* 16(12):1688-1689 (1966).

If there is a general mechanism by which thalidomide aids in the treatment of some cancers, its nature remains unclear. See, e.g., Moreira, A. L., et al., *J. Expr. Med.* 177:1675-1680 (1993); McHugh, S. M., et al., *Clin. Exper. Immunol.* 99:160-167 (1995); and Moller, D. R., et al., *J. Immunol.* 159:5157-5161 (1997). It has been reported, however, that thalidomide is an antiangiogenic agent that can suppress tumor necrosis factor α (TNF-α) and interleukin 12 (IL-12) production. See, e.g., Moller, D. R., et al., *J. Immunol.* 159:5157-5161 (1997); Moreira, A. L., et al., *J. Exp. Med.* 177:1675-1680 (1993); U.S. Pat. Nos. 5,593,990, 5,629,327, and 5,712,291 to D'Amato and U.S. Pat. No. 5,385,901 to Kaplan. And in vitro studies suggest that thalidomide affects the production of a variety of other proteins. See, e.g., McHugh, S. M., et al., *Clin. Exp. Immunol.* 99:160-167 (1995). Thalidomide may also affect mechanisms related to epithelial or endothelial function or growth. D'amato M., et al., *Proc. Natl. Acad. Sci.* 91:4082-4085(1994).

Given the great need for an effective and safe treatment of cancer, there continues to be an extensive amount of research on new drugs or ways of improving existing therapies. This invention addresses the need for a safe and effective treatment of colorectal cancer.

3. SUMMARY OF THE INVENTION

This invention is directed to pharmaceutical compositions, pharmaceutical dosage forms, kits, and methods of treating primary or metastatic colorectal cancer.

A first embodiment of the invention encompasses a method of treating primary and/or metastatic colorectal cancer, which comprises administering to a patient in need of such treatment a therapeutically effective amount of irinotecan, or a pharmaceutically acceptable prodrug, salt, solvate, hydrate, or clathrate thereof, and a therapeutically effective amount of thalidomide, or a pharmaceutically acceptable prodrug, salt, solvate, hydrate, or clathrate thereof.

In a preferred method of this embodiment, irinotecan is administered parenterally about every three weeks in an amount of from about 1 to about 1000 mg/m$^2$, preferably in an amount of from about 25 to about 750 mg/m$^2$, more preferably in an amount of from about 50 to about 500 mg/m$^2$, and most preferably in an amount of from about 100 to about 350 mg/m$^2$, and thalidomide is administered orally and daily in an amount of from about 1 to about 2000 mg, preferably from about 50 to about 1000 mg, more preferably from about 100 to 750 mg, and most preferably from about 200 to about 500 mg.

A second embodiment of the invention encompasses a pharmaceutical composition comprising irinotecan, or a pharmaceutically acceptable prodrug, salt, solvate, hydrate, or clathrate thereof, and thalidomide, or a pharmaceutically acceptable prodrug, salt, solvate, hydrate, or clathrate thereof.

A third embodiment of the invention encompasses a dosage form comprising irinotecan, or a pharmaceutically acceptable prodrug, salt, solvate, hydrate, or clathrate thereof, and thalidomide, or a pharmaceutically acceptable prodrug, salt, solvate, hydrate, or clathrate thereof.

A fourth embodiment of the invention encompasses a kit for use in the treatment or prevention of colorectal cancer which comprises a parenteral dosage form of irinotecan, or a pharmaceutically acceptable prodrug, salt, solvate, hydrate, or clathrate thereof, and an oral dosage form of thalidomide, or a pharmaceutically acceptable prodrug, salt, solvate, hydrate, or clathrate thereof.

4. DETAILED DESCRIPTION OF THE INVENTION

This invention encompasses pharmaceutical compositions, pharmaceutical dosage forms, kits, and methods of treating primary or metastatic colorectal cancer.

This invention is based, in part, on the unique ability of thalidomide to improve the overall therapeutic profile of irinotecan when used in the treatment of colorectal cancer. The invention consequently encompasses a method of treating or preventing colorectal cancer which comprises the administration of thalidomide, or a derivative, analogue, pharmaceutically acceptable prodrug, salt, solvate, hydrate, or clathrate thereof, in combination with irinotecan, or a pharmaceutically acceptable prodrug, salt, solvate, hydrate, or clathrate thereof, to a patient.

When used according to this invention, thalidomide can improve the efficacy of irinotecan at its common or approved dose. Thalidomide can further be used in combination with lower doses of irinotecan to reduce or avoid adverse affects associated with irinotecan while maintaining its efficacy. Thalidomide can also be used to reduce or avoid gastrointestinal toxicity caused by irinotecan. In short, this invention encompasses therapeutic effects that result from an unexpected and unique synergy between thalidomide and irinotecan. One of these therapeutic effects is an increased potency or efficacy of irinotecan; another is a reduced toxicity or increased safety of irinotecan.

Compositions of the invention include bulk drug compositions useful in the manufacture of pharmaceutical compositions (e.g., impure or non-sterile compositions), pharmaceutical compositions (i.e., compositions that are suitable for administration to a patient), and individual dosage forms. Each of the compositions and dosage forms of the invention comprise at least two of what are referred to herein as "active ingredients." A first active ingredient is irinotecan, or a pharmaceutically acceptable prodrug, salt, solvate, hydrate, or clathrate thereof. A second active ingredient is thalidomide, a derivative or analogue of thalidomide, or a pharmaceutically acceptable prodrug, salt, solvate, hydrate, or clathrate thereof.

Irinotecan contains a chiral center, and is commercially available as an optically pure compound. The methods and compositions of the invention encompass the use of racemic irinotecan, however, as well as enriched (i.e., uneven) mixtures of its enantiomers. Optically pure enantiomers of irinotecan can be prepared by methods well known in the art. These include, but are not limited to, resolution of chiral salts, asymmetric synthesis, or chiral chromatography. See generally, Beesley, T. E. and Scott, R. P. W., *Chiral Chromatography* (John Wiley & Sons, New York: 1999); *Principles of Asymmetric Synthesis,* Gawley, R. E. and Aube, J., eds. (Elsevier, Amsterdam: 1996); *Advanced Asymmetric Synthesis,* Stephenson, G. R., ed. (Chapman & Hall, London: 1996); and *Asymmetric Synthetic Methodology,* Ager, D. R. and East, M. B., eds. (CRC, Boca Raton: 1996). See also, Jacques, J., et al., *Enantiomers. Racemates and Resolutions* (Wiley-Interscience, New York: 1981); Wilen, S. H., et al., *Tetrahedron* 33:2725 (1977); Eliel, E. L. *Stereochemistry of Carbon Compounds* (McGraw-Hill, NY: 1962); and Wilen, S. H., *Tables of Resolving Agents and Optical Resolutions,* 268, Eliel, E. L., ed. (Univ. of Notre Dame Press, Notre Dame: 1972). It is further contemplated that pharmaceutically acceptable prodrugs of irinotecan be used in the methods and compositions of the invention.

Thalidomide contains a chiral center, and is sold as a racemate. The methods and compositions of the invention therefore encompass the use of racemic thalidomide as well as optically pure enantiomers of thalidomide. Optically pure enantiomers of thalidomide can be prepared by methods well known in the art. These include, but are not limited to, resolution of chiral salts, asymmetric synthesis, or chiral chromatography. It is further contemplated that pharmaceutically acceptable prodrugs, salts, solvate, clathrates and derivatives of thalidomide be used in the methods and compositions of the invention. Examples of derivatives of thalidomide that can be used in the methods and compositions of the invention include, but are not limited to, taglutimide, supidimide, and those disclosed by International Application WO 94/20085, which is incorporated herein by reference. Other derivatives of thalidomide encompassed by this invention include, but are not limited to, 6-alkyl-2-[3'- or 4'-nitrophthalimido]-glutarimides and 6-alkyl-3-phenylglutarimides. See e.g., De, A. U., and Pal. D., *J. Pharm. Sci.* 64(2): 262-266 (1975).

4.1. Methods of Treatment and Prevention

This invention encompasses methods of treating cancer of the colon and rectum mammals, and in humans in particular. Although dosage forms of the invention can be used in methods of the invention, the active ingredients disclosed herein can be administered separately, in any appropriate form, and by any suitable route.

Without being limited by theory, it is believed that the combined use of irinotecan and thalidomide to a patient suffering from colorectal cancer provides a unique and unexpected synergism. In particular, and without being limited by theory, it is believed that thalidomide can work in combination with irinotecan to more rapidly kill cancer cells, while at the same time reducing gastrointestinal (e.g., diarrhea) and other side effects associated with irinotecan.

Consequently, one embodiment of this invention encompasses methods of treating colorectal cancer, including primary and metastatic colorectal cancer, and preventing metastases of primary colorectal cancer, or preventing further colorectal metastasis. It further encompasses methods of treating patients who have been previously treated for cancer, as well as those who have not previously been treated for cancer. Indeed, the methods and compositions of this invention can be used in first-line and second-line cancer treatments. In a preferred embodiment, thalidomide is administered to a patient prior to the observation of intolerance of irinotecan.

Other embodiments of the invention include methods of increasing the dosage of irinotecan that can be safely and effectively administered to a patient, and methods of varying the dosage cycle used to administer irinotecan to a patient while avoiding dose-limiting toxicities.

This invention further encompasses methods of: 1) allowing the completion of chemotherapy in a greater percentage of patients; 2) avoiding deterioration of patients' nutritional status secondary to gastrointestinal toxicity; and 3) improving the overall quality of patients' life during chemotherapy.

4.1.1. Methods of Treating and/or Preventing Colorectal Cancer

The methods of treating and/or preventing colorectal cancer encompassed by this invention comprise administering at least two drugs (also referred to herein as "active ingredients"

or "active agents") to a patient (e.g., a human) suffering, or likely to suffer, from colorectal cancer: 1) irinotecan, or a pharmaceutically acceptable salt, solvate, clathrate, hydrate, or prodrug thereof, and; 2) thalidomide, a derivative or analogue of thalidomide, or a pharmaceutically acceptable salt, solvate, clathrate, hydrate, or prodrug thereof. The two active ingredients can be administered concurrently, sequentially, and by the same or by different routes of administration. For example, thalidomide can be administered to a patient prior to, during, or after the administration of irinotecan.

The magnitude of a prophylactic or therapeutic dose of each active ingredient in the acute or chronic management of colorectal cancer will typically vary with the specific active ingredients, the severity and type of cancer, and the route of administration. The dose, and perhaps the dose frequency, may also vary according to age, body weight, response, and the past medical history of the patient. Suitable dosing regimens can be readily selected by those skilled in the art with due consideration of such factors by following, for example, dosages reported in the literature and recommended in the *Physicial's Desk Reference®* (54$^{th}$ ed., 2000).

In one embodiment of the invention, irinotecan is administered parenterally about every three weeks in an amount of from about 1 to about 1000 mg/m$^2$, preferably in an amount of from about 25 to about 750 mg/m$^2$, more preferably in an amount of from about 50 to about 500 mg/m$^2$, and most preferably in an amount of from about 100 to about 350 mg/m$^2$. And in one embodiment of the invention, thalidomide is administered orally and daily in an amount of from about 1 to about 2000 mg, preferably from about 50 to about 1000 mg, more preferably from about 100 to 750 mg, and most preferably from about 200 to about 500 mg.

As noted elsewhere herein, this invention encompasses a method of reducing the time between therapeutically safe and effective doses of irinotecan. Consequently, in one specific embodiment of the invention, irinotecan is administered in a cycle of less than about three weeks (e.g., about once every two weeks, about once every ten days, or about once every week). The invention further allows the frequency, number, and length of irinotecan dosing cycles to be increased. Thus, another specific embodiment of the invention encompasses the administration of irinotecan for more cycles than are typical when it is administered alone. See, e.g., *Physicians' Desk Reference*, 2412-2418 (54$^{th}$ ed., 2000). In yet another specific embodiment of the invention, irinotecan is administered for a greater number of cycles that would typically cause dose-limiting toxicity in a patient to whom thalidomide is not also being administered.

In a typical embodiment of the invention, irinotecan is administered by intravenous infusion over about 90 minutes every cycle. In a specific embodiment, one cycle comprises the administration of about 125 mg/m$^2$ irinotecan on days 1, 8, 15, and 22, and then two weeks of rest. In another specific embodiment, each cycles comprises the administration of about 350 mg/m$^2$ of irinotecan, followed by three weeks of rest. Typically, the number of cycles during which irinotecan is administered to a patient will be from about 1 to about 12 cycles, more typically from about 2 to about 10 cycles, and even more typically from about 2 to about 8 cycles.

The dosage amounts and frequencies provided above are encompassed by the terms "therapeutically effective," "prophylactically effective," and "therapeutically or prophylactically effective" as used herein. When used in connection with an amount of a thalidomide or thalidomide derivative, these terms further encompass an amount of thalidomide or thalidomide derivative that reduces, prevents, or eliminates an adverse effect associated with the administration of irinotecan.

4.1.2. Methods of Increasing Irinotecan Dosages

This invention encompasses a method of increasing the dosage of irinotecan that can be safely and effectively administered to a patient. This method comprises administering to a patient (e.g., a human) thalidomide, or a pharmaceutically acceptable derivative, salt, solvate, clathrate, hydrate, or prodrug thereof. Patients that can benefit by this method are those likely to suffer from an adverse effect associated with irinotecan that is alleviated or reduced by the administration of thalidomide, or a pharmaceutically acceptable derivative, salt, solvate, clathrate, hydrate, or prodrug thereof, and which is of such severity that it would otherwise limit the amount of irinotecan that can be safely and effectively administered to them. Such adverse effects are referred to herein as "dose-limiting."

For example, adverse effects that are associated with irinotecan and which can limit the amount of irinotecan that can safely and effectively be administered to a patient include, but are not limited to, early and late-forming diarrhea, nausea, vomiting, anorexia, constipation, flatulence, leukopenia, anemia, neutropenia, asthenia, abdominal cramping, fever, pain, loss of body weight, dehydration, alopecia, dyspnea, insomnia, and dizziness.

According to a specific method of the invention, thalidomide, or a pharmaceutically acceptable derivative, salt, solvate, clathrate, hydrate, or prodrug thereof, is administered prior to, during, or after irinotecan. In one embodiment, thalidomide is administered orally and daily in an amount of from about 1 to about 2000 mg, preferably from about 50 to about 1000 mg, more preferably from about 100 to 750 mg, and most preferably from about 200 to about 500 mg.

4.2. Pharmaceutical Compositions and Dosage Forms

Pharmaceutical compositions can be used in the preparation of individual dosage forms. Consequently, pharmaceutical compositions and dosage forms of the invention comprise the active ingredients disclosed herein (i.e., irinotecan, or a pharmaceutically acceptable prodrug, salt, solvate, hydrate, or clathrate thereof, and thalidomide, a derivative or analogue of thalidomide, or a pharmaceutically acceptable prodrug, salt, solvate, hydrate, or clathrate thereof). Pharmaceutical compositions and dosage forms of the invention can further comprise one or more excipients.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences,* 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise thalidomide, a derivative or analogue of thalidomide, or a pharmaceutically acceptable salt, solvate, clathrate, hydrate, or prodrug thereof in an amount of from about 1 mg to about 2000 mg, more preferably from about 50 mg to about 1000 mg, even more preferably from about 100 mg to about 750 mg, and most preferably from about 200 mg to about 500 mg. Similarly, typical dosage forms of the invention comprise irinotecan or a pharmaceutically acceptable salt, solvate, clathrate, hydrate, prodrug or derivative thereof in an amount of from about 1 mg to about 1000 mg, more preferably from about 25 mg to about 750 mg, even more preferably from about 50 mg to about 500 mg, and most preferably from about 100 mg to about 350 mg.

4.2.1. Oral Dosage Forms

Pharmaceutical compositions of the invention that are suitable for oral administration can be presented as discrete dosage forms, such as, but are not limited to, tablets (e.g., chewable tablets), capiets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Typical oral dosage forms of the invention are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W. R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A preferred solid oral dosage form of the invention comprises thalidomide, anhydrous lactose, microcrystalline cellulose, polyvinylpyrrolidone, stearic acid, colloidal anhydrous silica, and gelatin.

4.2.2. Delayed Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

4.2.3. Parenteral Dosage Forms

Parenteral dosage forms can be administered to patients by various routes including, but not limited to, subcutaneous, intravenous, bolus injection, intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention. or example, cyclodextrin and its derivatives can be used to increase the solubility of halidomide and its derivatives. See, e.g., U.S. Pat. No. 5,134,127, which is incorporated herein by reference.

A preferred parenteral composition of the invention is intended for dilution with 5% Dextrose Injection, USP, or 0.9% Sodium Chloride Injection, USP, prior to administration to a patient, and is an aqueous solution that comprises irinotecan, sorbitol NF powder, and lactic acid, USP, and has a pH of from about 3.0 to about 3.8.

4.2.4. Transdermal, Topical, and Mucosal Dosage Forms

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences*, 16th and 18th eds., Mack Publishing, Easton Pa. (1980 & 1990); and *Introduction to Pharmaceutical Dosage Forms*, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., *Remington's Pharmaceutical Sciences*, 16th and 18th eds., Mack Publishing, Easton Pa. (1980 & 1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

4.2.5. Kits

Typically, active ingredients of the invention are preferably not administered to a patient at the same time or by the same route of administration. This invention therefore encompasses kits which, when used by the medical practitioner, can simplify the administration of appropriate amounts of active ingredients to a patient.

A typical kit of the invention comprises a dosage form of irinotecan, or a pharmaceutically acceptable prodrug, salt, solvate, hydrate, or clathrate thereof, and a dosage form of thalidomide, or a pharmaceutically acceptable derivative, prodrug, salt, solvate, hydrate, or clathrate thereof.

Kits of the invention can further comprise devices that are used to administer the active ingredients. Examples of such devices include, but are not limited to, syringes, drip bags, patches, and inhalers.

Kits of the invention can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

A specific kit of the invention comprises a solid dosage form of thalidomide suitable for oral administration to a patient, and a liquid dosage form of irinotecan suitable for dilution and parenteral administration to a patient. A preferred oral dosage form of thalidomide comprises 50 mg thalidomide, anhydrous lactose, microcrystalline cellulose, polyvinylpyrrolidone, stearic acid, colloidal anhydrous silica, and gelatin. A preferred liquid dosage form of irinotecan comprises 100 mg irinotecan hydrochloride, sorbitol NF powder, and lactic acid, USP, and has a pH of from about 3.0 to about 3.8.

5. EXAMPLES

Certain embodiments of the invention are illustrated by the following non-limiting examples.

5.1. Example 1

Treatment of Colorectal Cancer

A pilot clinical trial was conducted to investigate the safety and efficacy of administering thalidomide (400 mg/day, administered at bedtime) and irinotecan (325-350 mg/m$^2$ every 21 days) to patients with metastatic colorectal cancer. An interim analysis performed after enrollment of the first 9 patients on this protocol (2-8 cycles of irinotecan) revealed a remarkable absence of gastrointestinal toxicity typically associated with irinotecan. See Table 1. All patients were able to complete the prescribed chemotherapy regimen; only one patient required a 50% reduction of the irinotecan dose due to asthenia, and only one patient required a thalidomide dose reduction by 75% due to somnolence. Of the seven patients that could be evaluated, one went into complete remission, two attained partial remission, one had stable disease, and three progressed.

TABLE 1

Observed Toxicity Profile for Combination Therapy with Thalidomide and Irinotecan in 9 Patients with Metastatic Colorectal Cancer Compared with the Expected Toxicity Profile of Irinotecan Monotherapy

| | Expected (%) | | Observed (N) | | |
|---|---|---|---|---|---|
| Symptom | Grade 1-4 | Grade 3-4 | Grade 1-4 | Grade 3-4 | p |
| Nausea | 86.2 | 16.8 | 0 | 1 | <0.00001 |
| Vomiting | 66.8 | 12.5 | 0 | 0 | 0.00005 |

TABLE 1-continued

Observed Toxicity Profile for Combination Therapy with Thalidomide and Irinotecan in 9 Patients with Metastatic Colorectal Cancer Compared with the Expected Toxicity Profile of Irinotecan Monotherapy

| Symptom | Expected (%) | | Observed (N) | | p |
|---|---|---|---|---|---|
| | Grade 1-4 | Grade 3-4 | Grade 1-4 | Grade 3-4 | |
| Diarrhea (Late) | 87.8 | 30.6 | 1 | 0 | <0.00001 |
| Abdominal colic/pain | 23.7 | 2.3 | 0 | 0 | n.s |
| Constipation | 29.9 | 2.0 | 4 | 0 | n.s. |
| Asthenia | 75.7 | 12.2 | 6 | 0 | n.s. |

The p-values shown in Table 1 refer to the probability of observing the specified number of Grade 1-4 symptoms among 9 patients, given the expected frequencies of Grade 1-4 toxicity. Expected frequencies of toxicity were obtained from Rothenberg, M. L., et al., *J. Clin. Oncology* 14(4):1128-1135 (1996); Pitot, H. C., et al., *J. Clin. Oncology* 15(8):2910-2919 (1997); and Rothenberg, M. L., et al., *Cancer* 85(4): 786-795 (1999).

The complete absence of severe (grade 3-4) gastrointestinal toxicity in the patients used in the study is striking, statistically highly significant, and clinically very important.

The embodiments of the invention described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed is:

1. A method of reducing gastrointestinal toxicity associated with the administration of irinotecan in a human which comprises administering to a human in need of such reduction an effective amount of thalidomide.

2. The method of claim 1 wherein the thalidomide is administered prior to the administration of irinotecan.

3. The method of claim 1 wherein the thalidomide is administered concurrently with irinotecan.

* * * * *